United States Patent [19]

Weitz et al.

[11] Patent Number: 4,466,922

[45] Date of Patent: Aug. 21, 1984

[54] PREPARATION OF 3-ALKYL-3-ACYLOXY-4-HYDROXYBUT-1-ENES

[75] Inventors: Hans-Martin Weitz, Bad Durkheim; Rolf Fischer, Heidelberg, both of Fed. Rep. of Germany

[73] Assignee: BASF Aktiengesellschaft, Ludwigshafen, Fed. Rep. of Germany

[21] Appl. No.: 417,514

[22] Filed: Sep. 13, 1982

[30] Foreign Application Priority Data

Sep. 23, 1981 [DE] Fed. Rep. of Germany ....... 3137804

[51] Int. Cl.³ .............................................. C11C 3/02
[52] U.S. Cl. .................................. 260/410.9 R; 560/1; 560/93; 560/105; 560/112; 560/200; 560/240; 560/262
[58] Field of Search ................. 260/410.9 N, 410.9 Q; 560/240, 93, 200, 262, 1, 105, 112

[56] References Cited

U.S. PATENT DOCUMENTS

| | | | |
|---|---|---|---|
| 1,976,677 | 10/1934 | Wittwer | 560/240 |
| 3,227,747 | 1/1966 | Lum et al. | 260/410.9 N X |
| 3,433,824 | 3/1969 | Horsley | 560/93 X |
| 3,649,676 | 3/1972 | Galfré et al. | 560/240 |
| 3,661,980 | 5/1972 | Himmele et al. | 260/410.9 N X |
| 4,017,429 | 4/1977 | Steele et al. | 560/240 X |
| 4,044,041 | 8/1977 | Stapp | 260/410.9 N X |
| 4,115,415 | 9/1978 | Yoshihara et al. | 560/240 |
| 4,223,160 | 9/1980 | Hess | 560/240 X |
| 4,301,084 | 11/1981 | Laas et al. | 560/240 X |

FOREIGN PATENT DOCUMENTS

2620967 of 1976 Fed. Rep. of Germany .
8451475 of 1975 Japan .

OTHER PUBLICATIONS

J. Gen. Chem. USSR 13 (1943), 481.
Chemical Abstracts, 38, 3248, 1944.
J. Org. Chem. 35 (1970), 1839.
Berichte 66B (1933), 335.
J. Chem. Soc., Chem. Comm. 1972, p. 491.

*Primary Examiner*—Helen M. S. Sneed
*Attorney, Agent, or Firm*—John H. Shurtleff

[57] ABSTRACT

3-Alkyl-3-acyloxy-4-hydroxybut-1-enes are prepared by a process in which a 3-alkyl-3,4-epoxybut-1-ene is treated with a carboxylic acid and a copper salt of a carboxylic acid.

10 Claims, No Drawings

PREPARATION OF 3-ALKYL-3-ACYLOXY-4-HYDROXYBUT-1-ENES

The present invention relates to a process for the preparation of 3-alkyl-3-acyloxy-4-hydroxybut-1-enes by reacting a 3-alkyl-3,4-epoxybut-1-ene with a carboxylic acid.

It has been disclosed that, for example, 3-methyl-3,4-epoxybut-1-ene (isoprene epoxide) can be converted, in the presence of compounds of the formula R—OH (where R is hydrogen, alkyl or acyl) and/or mineral acids, to a variety of products. Thus, heating with water in the absence of an acid produces 2-methylcrotonaldehyde (tiglaldehyde) (J. Gen. Chem. USSR 13 (1943), 481 and C.A. 38, 3248). On the other hand, J. Org. Chem. 35 (1970), 1839 points out that 3-methyl-3,4-epoxybut-1-ene is converted in the presence of water to 3-methyl-3,4-dihydroxybut-1-ene, the conversion taking place even at room temperature.

Furthermore, it has been disclosed that 3-methyl-3,4-epoxybut-1-ene in water undergoes an exothermic rearrangement reaction in the presence of a mineral acid, in particular sulfuric acid, to give tiglaldehyde (Ber. 66B (1933), 335). 3-Methyl-3,4-epoxybut-1-ene also undergoes rearrangement in the presence of a rhodium(I) complex which acts as a weak Lewis acid, the product again being tiglaldehyde (J. Chem. Soc., Chem. Comm. 1972, page 491). 3-Methyl-3,4-epoxybut-1-ene is isomerized in the gas phase, in the presence of aluminum oxide or silicon dioxide (German Published Application DAS No. 2,620,967), to give tiglaldehyde, the reaction taking place at as low as 125° C. In contrast, in the presence of hydrobromic or hydroiodic acid and transition metal compounds dissolved in an organic solvent, 3-methyl-2,5-dihydrofuran is formed (U.S. Pat. No. 3,932,468).

Zh. Obsch. Khim. 27, page 2363 (C.A. 52, 7.145) discloses that 3-methyl-3,4-epoxybut-1-ene reacts with methanol in the presence of $BF_3$ etherate to give 3-methyl-3-methoxy-4-hydroxybut-1-ene.

If 3-methyl-3,4-epoxybut-1-ene in an organic solvent is treated with a lower carboxylic acid, eg. acetic acid, in the presence of an alkali metal iodide, 1-acetoxy-4-methyl-4-hydroxybut-2-ene is obtained (Japanese Preliminary Published Application No. 84.514/75).

It is an object of the present invention to prepare 3-alkyl-3-acyloxy-4-hydroxybut-1-enes in good yields from readily obtainable starting compounds.

We have found, surprisingly, that this object is achieved, and that 3-alkyl-3-acyloxy-4-hydroxybut-1-enes of the formula

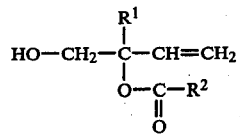
    I where $R^1$ is a hydrocarbon radical of 1 to 5 carbon atoms and $R^2$ is hydrogen or a hydrocarbon radical of 1 to 15 carbon atoms, can be prepared by a process in which a 3-alkyl-3,4-epoxybut-1-ene of the formula

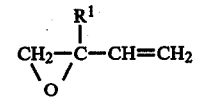
    II where $R^1$ has the above meanings, is treated with a carboxylic acid of the formula $R^2$—COOH, where $R^2$ has the above meanings, and with a copper salt of a carboxylic acid.

Suitable hydrocarbon radicals $R^1$ are, for example, alkyl, such as methyl, ethyl, propyl, butyl and pentyl, or alkenyl, such as propenyl and butenyl. Suitable hydrocarbon radicals $R^2$ are, for example, alkyl or alkylene radicals of 1 to 15 carbon atoms, benzyl and phenyl.

Where 3-methyl-3,4-epoxybut-1-ene and acetic acid are used, the reaction can be represented by the following equation:

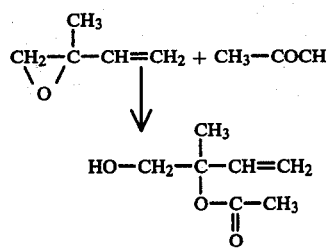

On the basis of the prior art, it was not possible to predict whether the main product of the reaction, in accordance with the invention, of 3-methyl-3,4-epoxybut-1-ene with a moderately strong acid, eg. acetic acid, would be tiglaldehyde, 3-methyl-2,5-dihydrofuran, 3-methyl-1-acetoxy-4-hydroxybut-2-ene or the desired product 3-methyl-3-acetoxy-4-hydroxybut-1-ene.

Examples of suitable starting materials of the formula II are 3-methyl-, 3-ethyl-, 3-n-propyl-, 3-i-propyl-, 3-n-butyl-, 3-tert.-butyl-, 3-n-pentyl-, 3-propenyl- and 3-butenyl-3,4-epoxybut-1-ene.

The above starting compounds II can be prepared, for example, by epoxidizing the corresponding 1,3-diene with a per-acid (German Laid-Open Application DOS No. 2,734,242), with a hydroperoxide (J. Org. Chem. 35 (1970), 1839), or with hydrogen peroxide (German Published Application DAS No. 2,012,049), or according to the halohydrin method (J. Org. Chem. 25 (1960), 1673).

Examples of suitable carboxylic acids are formic acid, acetic acid, propionic acid, butyric acid, valeric acid, caproic acid, lauric acid, oleic acid, palmitic acid, cyclohexanecarboxylic acid, benzoic acid and phenylacetic acid. Suitable copper salts are those of the above carboxylic acids.

In a preferred embodiment of the process, the epoxide is added to the liquid carboxylic acid, and the reaction is carried out at a temperature from the solidification point of the particular carboxylic acid to 90° C. and in the presence of a copper salt of a carboxylic acid. This procedure suppresses the formation of tiglaldehyde (see the experimental results in the Table). A mixture of the particular carboxylic acid with a solvent which is inert under the reaction conditions can be used, since this mixture has a lower solidification point than that of the carboxylic acid itself.

The reaction can, for example, be carried out as follows: the particular carboxylic acid, which when it is used in excess can simultaneously serve as the solvent, is brought to the particular reaction temperature, and the epoxide and the copper salt are then added. After the required reaction time, the unreacted carboxylic acid is distilled off and the residue is fractionally distilled to obtain the 3-alkyl-3-acyloxy-4-hydroxybut-1-ene.

The reaction is carried out, for example, at from −20° to 150° C., in particular from 0° to 90° C., under atmospheric or superatmospheric pressure, for from 0.5 to 20 hours. Advantageously from 1 to 30, in particular from 1.1 to 20, moles of the carboxylic acid are employed per mole of the epoxide. For example, from 0.01 to 1, in particular from 0.05 to 0.2, mole of one of the above copper salts is employed per mole of epoxide.

Examples of solvents which are inert under the reaction conditions and which are used in particular in the case of high-melting carboxylic acids are carboxylates, eg. methyl acetate, chlorohydrocarbons, eg. methylene chloride, chloroform, carbon tetrachloride and 1,2-dichloroethane, hydrocarbons, eg. alkanes, alkenes, alkynes, benzene and alkylbenzenes, and ethers, eg. diethyl ether, tetrahydrofuran and dioxane. From 0.01 to 30, in particular from 0.1 to 20 moles of the particular solvent are used per mole of starting compound.

The 3-alkyl-3-acyloxy-4-hydroxybut-1-enes obtainable by the process of the invention are useful starting materials for the preparation of crop protection agents, drugs or vitamin intermediates. Thus, for example, 3-methyl-3-acetoxy-4-hydroxybut-1-ene can be oxidized to 2-methyl-2-acetoxybut-3-enal, which can undergo rearrangement, as described in German Published Application DAS No. 1,297,597 and German Laid-Open Application DOS No. 2,840,125, to give the vitamin A intermediate 2-methyl-4-acetoxybut-2-enal. The same starting material, when the acetoxy group is hydrolyzed and the primary OH group oxidized, gives vinyllactic acid, which is an intermediate for an important fungicide (German Laid-Open Application DOS No. 2,207,576).

EXAMPLES 1 TO 15

(Examples 1, 3, 5, 6, 7, 8, 10, 12, 14 and 15 are comparative examples.)

The 3-methyl-3,4-epoxybut-1-ene used is prepared as described in J. Org. Chem. 25, pages 1673 et seq. 8.4 g of 3-methyl-3,4-epoxybut-1-ene are added dropwise, in the course of 10 minutes, at the stated temperature and while stirring, to 100 g of glacial acetic acid which may or may not contain dissolved additives (see the Table). Stirring is continued for 30 minutes at this temperature, after which the product is analyzed by gas chromatography (4 m Carbowax 20M column). The composition of the reaction mixture is given in the Table.

EXAMPLE 16

50.4 g of 3-methyl-3,4-epoxybut-1-ene are added dropwise, in the course of 30 minutes, at 25±2° C. and while stirring, to 150 g of glacial acetic acid, in which 12 g of $Cu(CH_3COO)_2 \cdot H_2O$ are dissolved. Stirring is continued for 2 hours at this temperature, and the excess acetic acid is then stripped off in a rotary evaporator, under reduced pressure from a water jet. Fractional distillation of the residue gives 59.7 g (69%, based on epoxide employed) of 3-methyl-3-acetoxy-4-hydroxybut-1-ene of boiling point 74° C./13 mbar and $n_D^{20} = 1.4418$.

TABLE

Reaction of 3-methyl-3,4-epoxybut-1-ene with acetic acid in the presence and absence of copper salts

| Experiment No. | Temperature [°C.] | Additive [g] | I | II | III | IV | tiglaldehyde |
|---|---|---|---|---|---|---|---|
| | | | Mole-%, based on 3-methyl-3,4-epoxybut-1-ene employed | | | | |
| 1[1] | 10 | — | 52 | 0.1 | 15 | 0.2 | 13 |
| 2[1] | | 2 g $Cu(OAc)_2 \cdot H_2O$ | 75 | 0.3 | 8 | 0.1 | 6 |
| 3 | 25 | — | 52 | 0.2 | 16 | 0.2 | 15 |
| 4 | | 2 g $Cu(OAc)_2 \cdot H_2O$ | 74 | 2 | 8 | 0.1 | 5 |
| 5 | | 2.4 g $Cu(NO_3)_2 \cdot 3H_2O$ | 56 | 1 | 8 | 0.5 | 11 |
| 6 | | 1.9 g CuI | 58 | 1 | 17 | 0.2 | 14 |
| 7 | | 0.98 g KOAc | 53 | 0.4 | 18 | 0.1 | 16 |
| 8 | 40 | — | 51 | 0.2 | 16 | 0.2 | 17 |
| 9 | | 2 g $Cu(OAc)_2 \cdot H_2O$ | 58 | 9 | 12 | 0.2 | 6 |
| 10 | 60 | — | 50 | 0.1 | 17 | 0.2 | 20 |
| 11 | | 2 g $Cu(OAc)_2 \cdot H_2O$ | 57 | 17 | 10 | 0.4 | 4 |
| 12 | 80 | — | 49 | 0.1 | 17 | 1 | 23 |
| 13 | | 2 g $Cu(OAc)_2 \cdot H_2O$ | 57 | 19 | 8 | 1 | 4 |
| 14 | 100 | — | 44 | 0.5 | 15 | 3 | 27 |
| 15 | 118 | — | 37 | 2 | 12 | 9 | 32 |

[1] The 100 g of acetic acid contain 10% by weight of ethyl acetate.
I = 3-methyl-3-acetoxy-4-hydroxybut-1-ene
II = 3-methyl-3,4-diacetoxybut-1-ene
III = cis- and trans-2-methyl-1-hydroxy-4-acetoxybut-2-ene
IV = cis- and trans-2-methyl-1,4-diacetoxybut-2-ene
V = 2-methylcrotonaldehyde (tiglaldehyde)

We claim:
1. A process for the preparation of a 3-alkyl-3-acyloxy-4-hydroxybut-1-ene of the formula

$$HO-CH_2-\underset{\underset{\underset{O}{\overset{\|}{C}}-R^2}{|}}{\overset{R^1}{\underset{|}{C}}}-CH=CH_2 \quad I$$

where $R^1$ is a hydrocarbon radical of 1 to 5 carbon atoms and $R^2$ is a hydrogen or a hydrocarbon radical of 1 to 15 carbon atoms, which process comprises reacting a 3-alkyl-3,4-epoxybut-1-ene as an epoxide of the formula

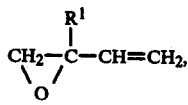

where $R^1$ has the above meanings, with from 1.1 to 20 moles per mole of the epoxide II of a carboxylic acid of the formula $R^2$—COOH, where $R^2$ has the above meanings, at a temperature of from $-20°$ to $150°$ C. and in the presence of from 0.01 to 1 mole per mole of the epoxide II of a copper salt of a carboxylic acid of the formula $R^2$—COOH, where $R^2$ has the above meanings.

2. A process as claimed in claim 1, wherein the reaction is carried out at from 0° to +90° C.

3. A process as claimed in claim 1, wherein said carboxylic acid $R_2$—COOH is a member selected from the group consisting of formic acid, acetic acid, propionic acid, butyric acid, valeric acid, caproic acid, lauric acid, oleic acid, palmitic acid, cyclohexanecarboxylic acid, benzoic acid and phenylacetic acid.

4. A process as claimed in claim 1, wherein said carboxylic acid is acetic acid.

5. A process as claimed in claim 1, wherein the carboxylic acid reactant is employed in an amount of from 1.1 to 20 moles per mole of the epoxide II.

6. A process as claimed in claim 1, wherein the copper salt is present in an amount of from 0.05 to 0.2 mole per mole of the epoxide II.

7. A process as claimed in claim 1, wherein the reaction is carried out with an inert organic solvent for the carboxylic acid being reacted, using the solvent in an amount of from 0.01 to 30 moles per mole of the starting compound.

8. A process as claimed in claim 7 wherein the inert solvent is used in an amount of from 0.1 to 20 moles per mole of the starting compound.

9. A process as claimed in claim 1, using the carboxylic acid reactant in an amount of from 1.1 to 20 moles per mole of the epoxide II, and using the copper salt of the same carboxylic acid reactant in an amount of from 0.05 to 0.2 mole per mole of the epoxide II.

10. A process as claimed in claim 9, wherein the carboxylic acid is acetic acid.

* * * * *